(12) United States Patent
Wold

(10) Patent No.: US 6,562,567 B2
(45) Date of Patent: May 13, 2003

(54) METHOD OF DETECTING A NUCLEIC ACID

(75) Inventor: Barbara J. Wold, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/238,528

(22) Filed: Jan. 27, 1999

(65) Prior Publication Data

US 2002/0098478 A1 Jul. 25, 2002

Related U.S. Application Data

(60) Provisional application No. 60/072,643, filed on Jan. 27, 1998.

(51) Int. Cl.[7] ............................ C12Q 1/68; C12P 19/34; C07H 21/02; C07H 21/04
(52) U.S. Cl. ............................ 435/6; 435/91.2; 935/77; 935/78; 536/23.1; 536/25.32
(58) Field of Search ...................... 435/6, 91.2; 935/77, 935/78; 536/23.1, 25.32

(56) References Cited

U.S. PATENT DOCUMENTS

| 5,547,835 A | 8/1996 | Köster ........................... 435/6 |
| 5,639,603 A | 6/1997 | Dower et al. ................... 435/6 |
| 5,770,367 A | 6/1998 | Southern et al. ............... 435/6 |
| 6,027,890 A | * 2/2000 | Ness et al. ...................... 435/6 |

FOREIGN PATENT DOCUMENTS

| WO | WO 95/04160 | 2/1995 | ............ C12Q/1/68 |

* cited by examiner

*Primary Examiner*—Gary Benzion
*Assistant Examiner*—Joyce Tung
(74) *Attorney, Agent, or Firm*—Gray Cary Ware & Freidenrich, LLP; Lisa A. Haile; Emanuel J. Vacchiano

(57) ABSTRACT

Disclosed is a method of detecting specific nucleic acids using an oligonucleotide linked to a cleavable tag. The presence of a specific nucleic acid in a population of nucleic acids is determined by hybridizing an oligonucleotide containing the tag to a population of nucleic acids, separating hybridizing bound oligonucleotides, and then removing and identifying the tag. Also provided are compositions and kits comprising oligonucleotides linked to a cleavable tag.

16 Claims, 3 Drawing Sheets

Step 1. Assemble reaction mixture. Here consisting of detector primers 1-3 and target RNAs 1,2,4

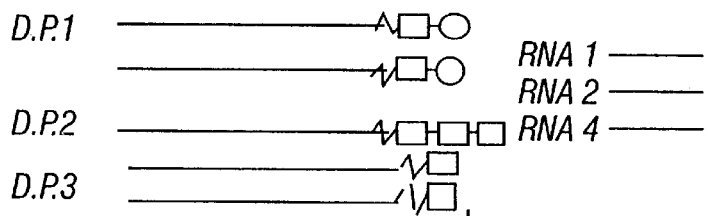

Step 2. React under favorable annealing condition

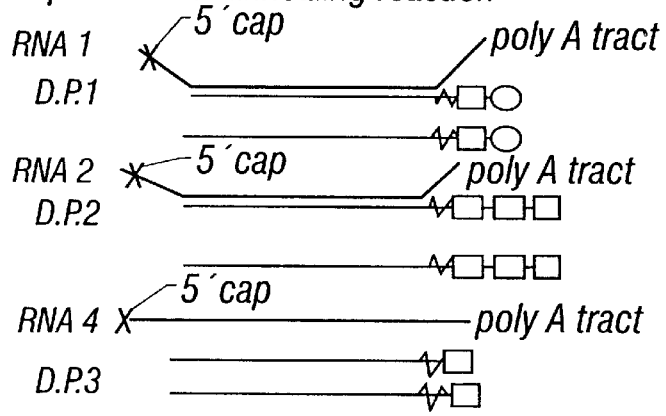

Step 3. Separate hybridized detector oligonucleotides from unhybridized ones example: via poly A affinity chromatography Retain Poly A positive fraction including RNA4 and duplexes of RNA2 and D.P.2 and RNA1 and D.P.1

Discard poly A negative including all D.P.3 and the unhybridized D.P.1

Retained Poly A positive RNA plus poly A RNA/detecto oligonucleotide heteroduplexes Step 4: Cleave (or photocleave) mass tags from their respective oligos: separate liberated tags from bound RNA and RNA/oligo duplexes Retained RNA, oligos Discard Released mass tags to mass spec analyzer

*FIG. 2*

METHOD OF DETECTING A NUCLEIC ACID

CROSS REFERENCE TO RELATED APPLICATIONS

This application claims priority under 35 USC §119(e)(1) from U.S. Serial No. 60/072,643 (herein incorporated by reference), which was filed Jan. 27, 1998.

FIELD OF THE INVENTION

The present invention relates generally to the field of nucleic acid detection and specifically to a method for identifying a specific nucleic acid in a population of nucleic acids using a cleavable molecular tag linked to an oligonucleotide.

BACKGROUND OF THE INVENTION

An important part of functional genomics is the analysis of gene transcription in a large population of nucleic acids. Transcription analysis can potentially allow for the determination the identity of each gene expressed in a cell and the relative amount of transcript expressed compared with a control sample. Such analyses can thus reveal the "gene state" of a cell type or organism. However, quantitative analyses of transcription levels in a cell can be limited by the relatively large amount of the input RNA sample material needed, and by the wide variation in the abundance of different transcripts in a population of nucleic acid molecules, e.g., in the relative abundance of RNA molecules present in a single cell. The relative abundance, or dynamic range, can vary about four logs (10,000-fold) in RNA from populations of homogeneous cells or single cell assays. The range may vary for an additional three orders or more of magnitude for heterogenous cell samples.

There exists a need for a method detecting specific nucleic acid sequences in small amounts of a population of nucleic acid sequence, and whose abundance can vary over several orders of magnitude.

SUMMARY OF THE INVENTION

The invention is based on the discovery that cleavable tags attached to oligonucleotides can be used to identify specific nucleic acids in a population or collection of nucleic acids. In the methods described herein, tagged oligonucleotides are hybridized with a population or collection of nucleic acids. Hybridized oligonucleotides are then separated from non-hybridized oligonucleotides, and the tag is cleaved from the hybridized oligonucleotide and its identity determined. The identity of the tag thus reveals the identity of the oligonucleotide and the nucleic acid in the population or collection of nucleic acids to which the oligonucleotide hybridized.

The invention provides methods of detecting a specific nucleic acid in a population or collection of nucleic acids. In other embodiments, the invention provides compositions of tagged oligonucleotides and kits comprising tagged oligonucleotides for detecting specific nucleic acid sequences.

Among the advantages of the invention is increased sensitivity in detecting specific nucleic acid sequences in small amounts of an input population or collection of nucleic acid sequences. Another advantage of the invention is the ability to detect nucleic acids whose relative abundance may differ over several orders of magnitude in a nucleic acid sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following description, and from the claims.

BRIEF DESCRIPTION OF THE DRAWINGS

FIG. 2 shows a schematic drawing of a method of detecting a specific transcript using a detector oligonucleotide.

DESCRIPTION OF THE PREFERRED EMBODIMENTS

The present invention provides a rapid, quantitative process for detecting a specific nucleic acid sequence in a population or collection of nucleic acid sequences. The method is based on the use of a tagged oligonucleotide that is complementary to at least a portion of a specific nucleic acid sequence in the population or collection of nucleic acid whose presence or abundance is to be assessed.

Figure 1:
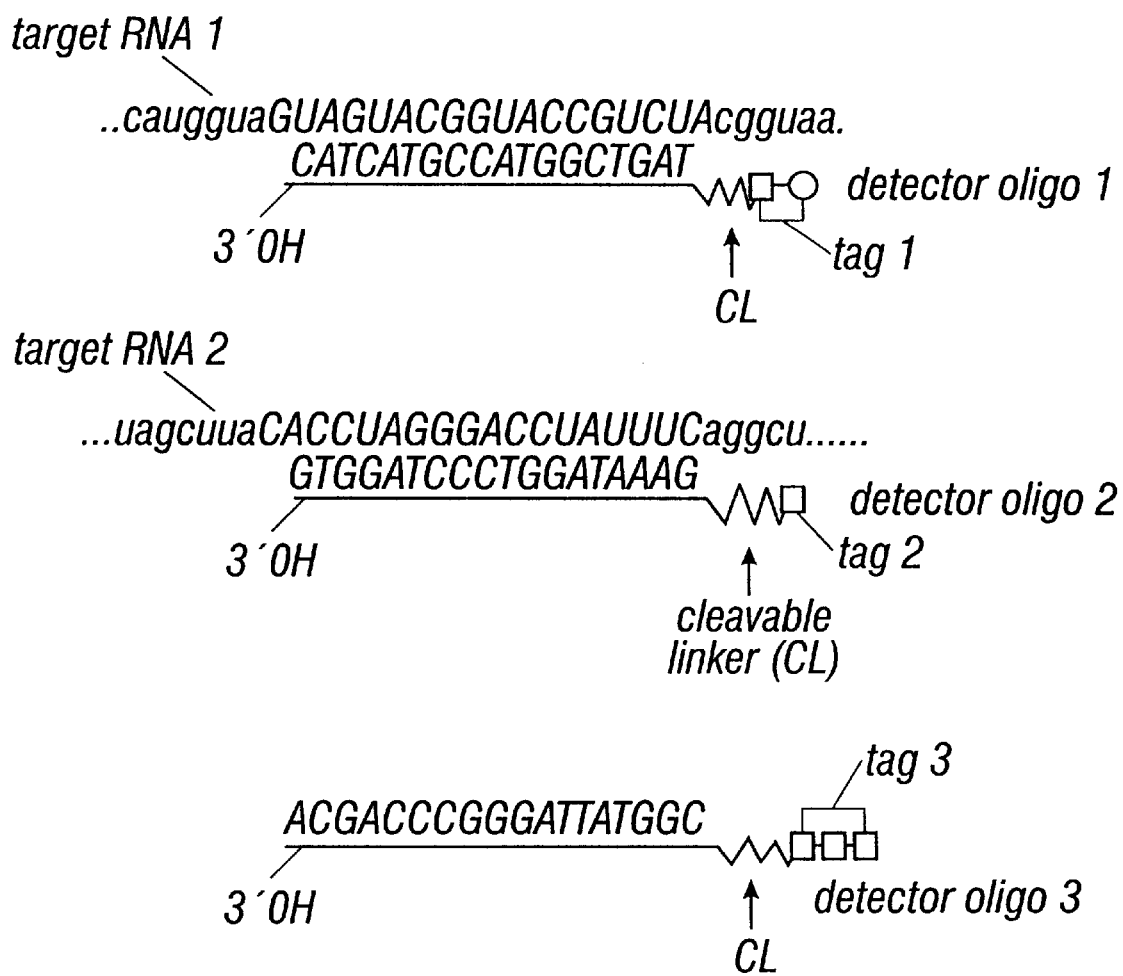
FIG. 1 shows a schematic drawing of tagged oligonucleotides having a nucleic acid sequence, which is complementary to at least a portion of a desired target sequence, linked to a tag moiety via a cleavable linker.

Three tagged oligonucleotides according to the invention are illustrated in FIG. 1, where they are labeled detector primer 1, detector primer 2, and detector primer 3. Each detector primer includes a specified oligonucleotide sequence attached to tags 1–3, respectively, via a cleavable linker (CL). Two of the detector primers shown have complementary sequences in a population of target RNAs.

The detection of specific nucleic acid sequences using detector primers is shown schematically in FIG. 2. In the first step, detector primers 1–3 are mixed with a population of target RNAs. For each specific nucleic acid sequence to be detected, one or more selector oligonucleotides are designed to specifically anneal with a desired target nucleic acid.

Step 2 illustrates the results of annealing the detector primers to the target nucleic acids to form a mixture of hybridized and non-hybridized oligonucleotides. In step 3, the hybridized detector oligonucleotides are separated from the non-hybridized oligonucleotides. The presence of the polyA$^+$-tract on target RNAs is used in this example to separate polyA$^+$-containing RNA molecules bound to the detection primers from non-hybridized detection primers and nucleic acids lacking a polyA$^+$ region.

The linker is cleaved in step 4 to release the tag from the oligonucleotide. In steps 5 and 6, the released tag is purified, if necessary, and its identity determined. In the example shown, the tag is identified using mass spectrometry. The example illustrates that it is the tag itself, rather than the oligonucleotide, that is ultimately detected. By identifying and quantitating the tags associated with primers that anneal stably, as opposed to tags from oligonucleotides that do not anneal, it is possible to indirectly but quantitatively score the presence and amount of the target nucleic acid.

A single hybridization reaction will typically contain multiple different detector oligonucleotides corresponding to different target nucleic acids. The different target sequences, as is explained in more detail below, can be, for example, different RNAs or different sequences within the same RNA. When the tag is detected using mass spectrometry, very high level multiplexing is possible because of the ability of the mass spectrometry to discriminate tags differing from each other by small mass increments.

At the end of this process, it is possible to deduce whether a particular nucleic acid sequence, e.g., an RNA sequence or DNA sequence was present in the original sample collection of nucleic acids, e.g,. DNA or RNA from a cell lysate, RNA preparation, or other biological sample containing RNA or a nucleotide representation of the RNA such as cDNA, by the presence of the tag corresponding to the tagged oligonucleotide. The presence and the absolute and/or the relative amount of a given tag reflects the amount of the target complementary nucleic acid present in the original sample.

The range of quantitation possible will depend on how the annealing reactions are constructed and executed, on the choice of tags and on details of the particular methodology used to distinguish the tags. Depending on the specific use, the design parameters can be varied to favor diversity of target, sensitivity, and dynamic range. For example, multiple different oligonucleotides with distinct tags directed at different parts of the same gene or RNA can be used as informative internal controls. Similarly, if the same tag is used for multiple oligonucleotides directed at the same target nucleic acid, one can elevate sensitivity, as for a rare target RNA. Thus, the present invention provides a way to detect specific target sequences using small amount of starting material, and to examine levels of both rare and abundant nucleic acid sequences in a collection of nucleic acid sequences.

In a first embodiment, the invention provides a method for the detection of a specific nucleic acid sequence, or target sequence, in a collection, or sample, of nucleic acid sequences. The collection of nucleic acid sequences can include, e.g, DNA, RNA, or a mixture of DNA and RNA, and can be from a cell, either prokaryotic or eukaryotic, or non-cellular agent such as a virus or viroid. The target source can be within a mRNA, hnRNA, rRNA, tRNA, or snRNA, or within DNA, e.g., nuclear, mitochondrial, chloroplast DNAs, as well as plasmid DNAs.

The collection of nucleic acids can be from one source, or from one or more sources, e.g., DNA from a single individual, a mixture of two or more individuals, or a mixture of cell types from the same individual. Alternatively, the collection can include RNA from a particular cell, tissue, or cell extract, including at a particular physiological state, developmental stage, or in a particular disease extract.

The method includes providing at least one oligonucleotide, also termed the "detector oligonucleotide", covalently linked to a removable tag, which is also referred to herein as a "tagged oligonucleotide." The identity of both the tag and oligonucleotide sequence to which the tagged attached is known.

The term "tag" as used herein refers to a chemical moiety that can be detected and quantified. In preferred embodiments the tag is detected and quantified using mass spectrometry. While the tag need not have a particular type of chemical structure, it must be stable while the linked oligonucleotide is hybridized to the target nucleotide sequence. Preferably, the tag is also stable upon long term storage and is linked to the oligonucleotide so that its subsequent removal is simple, efficient, and can be occur without rendering the tag non-identifiable. Examples of tags include, e.g., amino acids, small peptides composed of 2–20 amino acids, and polymers with different numbers of methyl groups or other simple repeating units.

The term "oligonucleotide" as used herein refers to primers or oligomer fragments comprised of two or more deoxyribonucleotides or ribonucleotides, preferably more than three. The exact size will depend on many factors, which in turn depend on the ultimate function or use of the oligonucleotide. In some embodiments, the oligonucleotide is, e.g., 8–50 nucleotides, 15–45 nucleotides, or 17–35 nucleotides in length.

The method also includes contacting the oligonucleotide with a collection of nucleic acid sequences under conditions which permit hybridization of the oligonucleotide to a complementary sequence in the collection of nucleic acid sequences, to form a mixture of hybridized and non-hybridized oligonucleotides. The contacting step is typically conducted with the annealing of the tagged oligonucleotide with the collection of nucleic acids under conditions of molar excess of oligonucleotide to target, and other kinetic conditions such that the annealing is stopped near or beyond kinetic termination. The hybridization reactions can be done in either solid phase or solution, but for many applications solution hybridization will be preferable because the reactions can readily be driven to kinetic completion and to target saturation.

In some applications the oligonucleotide will have perfect complementary, or nearly perfect complementary, to a region of a target sequence in a collection of nucleic acids. This will be desirable when the target sequence differs by only one or a few nucleotides in sequence from other sequences in a collection of nucleic acid sequences. This situation can arise, for example, when distinguishing two alleles of a gene that may differ from one another in a single nucleotide sequence. For other applications, perfect complementary between the oligonucleotide sequence and a target sequence will not be necessary.

The method also comprises separating hybridized oligonucleotides from non-hybridized oligonucleotides. Separation can be done in any of several methods and, depending on the desired level of sensitivity, can be designed to be more or less stringent for eliminating nonhybridized material. Higher stringency conditions will generally be required if, for example, the tagged oligonucleotide sequence differs by only one or a few nucleotides from non-target sequences in the collection of nucleic acid sequence, e.g., when the tagged oligonucleotide is used to distinguish alleles of a gene which differ in single nucleotide. Higher stringency conditions will also be desirable when a small amount of the target nucleic acid is present, while lower stringency conditions may be acceptable when large amounts of the target nucleic acid is present, or when the signal to noise ratio is otherwise high.

While the method is not limited to a particular scheme for separating hybridized and non-hybridized oligonucleotides, it is important that the separation scheme be compatible with the chemical properties of the tags, i.e., the separation step must not alter the tag such that the tag cannot be identified subsequently.

In some embodiments, structural features found on some nucleic acid molecules can be used to separate bound and unbound oligonucleotides. One such separation procedure based on detecting polyA$^+$ sequences in mRNA and is shown schematically in FIG. 2. Most mRNAs in eukaryotic cells have a polyA$^+$ tract at their 3' end, and methods for purification on the basis of the presence of polyA$^+$ tract are well established and simple. In this example, all RNA containing polyA$^+$, as well as those detector oligonucleotides that are stably associated with RNA, are removed from nonhybridized oligonucleotides because the hybridized oligonucleotides co-enrich with the polyA$^+$ RNA.

The separation can be further enhanced, with a resulting increase in purification and downstream increase in signal to noise ratios, by combining the poly A$^+$ selection with another selection method, e.g., a method based on recognizing 5' cap structures on some eukaryotic mRNAs. Other methods of enhancing separation are by performing multiple iterations of the selection, or by using selection with a second oligonucleotide termed the selector oligonucleotide, which is explained in more detail below.

Also included in the method of the invention is removal of the tag from the hybridized oligonucleotides. Tags can be removed from their respective oligonucleotides by methods known in the art, e.g., by appropriate chemical (or photochemical) reaction (indicated by the arrow in FIG. 1).

The method also includes identification of the cleaved tag. The tag can be identified by any of several methods, including mass spectra, emission spectra, absorption spectra, and antibody-binding. In preferred embodiments the tag is identified by mass spectrometry.

The mass spectrophotometric method can be, e.g., time-of-flight, quadrupole, magnetic sector or ion trap mass spectrometry.

Because the tag and oligonucleotide to which the tag is originally linked is known, determining the identity of the detached tag makes it possible to deduce whether a nucleic acid sequence complementary to the oligonucleotide sequence was present in the sample.

The number of nucleic acid sequences analyzed can be increased by using at least two distinct tagged oligonucleotides, i.e., tagged oligonucleotides having distinguishable tags. These tags will typically also be attached to oligonucleotides that have distinguishable sequences. Multiple tagged oligonucleotides makes it possible to determine the relative amount of two target nucleic acid sequences by measuring the relative amounts of their corresponding tags. In general, the range of quantitation possible will depend on how the annealing reactions are performed, the choice of the mass tags, and on the particular detection methodology used. Depending on the particular target, sensitivity required, or the dynamic range examined, it is possible to detect or quantitate sequences corresponding to different parts of a single nucleic acid molecule, e.g., of parts of a single RNA molecule.

In general, multiple oligonucleotides with distinct tags complementary to different parts of the same gene or RNA can be used as informative internal controls. Alternatively, if the same tag is used on multiple oligonucleotides, each of which is complementary to different regions of the same target sequence, then one tag can be used to identify a single target nucleic acid. The additive use of multiple tagged oligonucleotides can enhance detection of nucleic acids occurring in low abundance in the target collection of nucleic acid molecules. Conversely, a small number of tagged oligonucleotides may be used to identify a target sequence abundant in the target population. Altering the number of oligonucleotides is a way to minimized problems of initial sensitivity and undesirably high dynamic range. This method can also be used in other situations where there is a large difference in the abundance of two target sequences in a collection of nucleic acids. For example, the method can be used to measure the relative amounts of intron versus exon sequence for a single gene, or to detect the relative amount of 5' end sequence versus 3' end sequence of a particular transcript, or to determine the relative abundance of one allele of a gene compared to a second in a population.

Additional diversity in the tagged oligonucleotides can be generated by varying the linkage between the tag and the oligonucleotide. For example, two tagged oligonucleotide families can be prepared using a photoabile linker "x" or a photolabile linker "y. " The linkers will differ in the wavelength at which they are cleaved. One set of tagged oligonucleotides can be constructed having tags a, b, and c, linked via "x" to oligonucleotides 1, 2, 3, respectively. A second set of oligonucleotides is constructed having tags a, b, and c linked via "y" to oligonucleotides 4, 5, and 6. Liberation of tag a at the "x"-responsive wavelength reveals the presence of a nucleic acid complementary to oligonucleotide 1, while liberation of tag a following irradiation at the "y"-responsive wavelength indicates the presence of a nucleic acid homologous to the oligonucleotide 4. Thus, varying the linkage between the oligonucleotide and the tag allows for a relatively small number of tags to be used to identify multiple nucleic acids.

In another embodiment of the invention, the first oligonucleotide, or detector oligonucleotide, is provided along with a second tagged oligonucleotide, which is also referred to herein as the "selector oligonucleotide." The selector oligonucleotide is designed to hybridize specifically with the target nucleic acid sequence at a specifically selected position other than that of the detector oligonucleotide. The selector oligonucleotide is chosen so that it can be joined to the detector oligonucleotide directly in a subsequent ligation step, or so that it can be used along with the detector oligonucleotide to create an amplification product requiring both the detector oligonucleotide and the selector oligonucleotide.

The selector oligonucleotide thus acts to increase the specificity of detection for detector oligonucleotides that are correctly hybridized to their intended target nucleic acids compared to any less specific interactions of detector oligonucleotides with non-target RNAs, which might correspond to truly nonspecific background or might be members of related but non-identical genes within a gene family. While it will often be desirable to use a selector oligonucleotide will be most preferable when detecting a target nucleic acid in very small amounts of starting material, it can also be used when there are larger amounts of starting material.

Unlike the detector mass tags, however, the selector tag need not be different for each target RNA or gene to be assayed. Instead, it can be universal for a large family, or library, of corresponding detector oligonucleotides. Thus, in the simplest case only one selector tag will be used for all target RNAs or genes in a reaction. However, it is readily apparent that increasing the number of detector oligonucleotides will increase the number of sequences detectable using selector oligonucleotides. Moreover, diversity can be increased by using a limited number of selector tags in combination with a limited number of detector tags.

The precise position of the selector oligonucleotide relative to the detector oligonucleotide, and its "sense" relative to the detector oligonucleotide and the target nucleic acid, will depend on the precise chemical nature of the oligonucleotides (DNA or RNA or other) and on whether a ligation reaction or a polymerization reaction is to be used in the subsequent steps.

A selector oligonucleotide in addition offers a facile handle for retrieving and physically separating properly hybridized detector oligonucleotides though their physical linkage to a companion selector oligonucleotide, e.g., in using ligase chain reaction or polymerase chain reactions based on the selector oligonucleotide and detector oligonucleotide.

Figure 3:
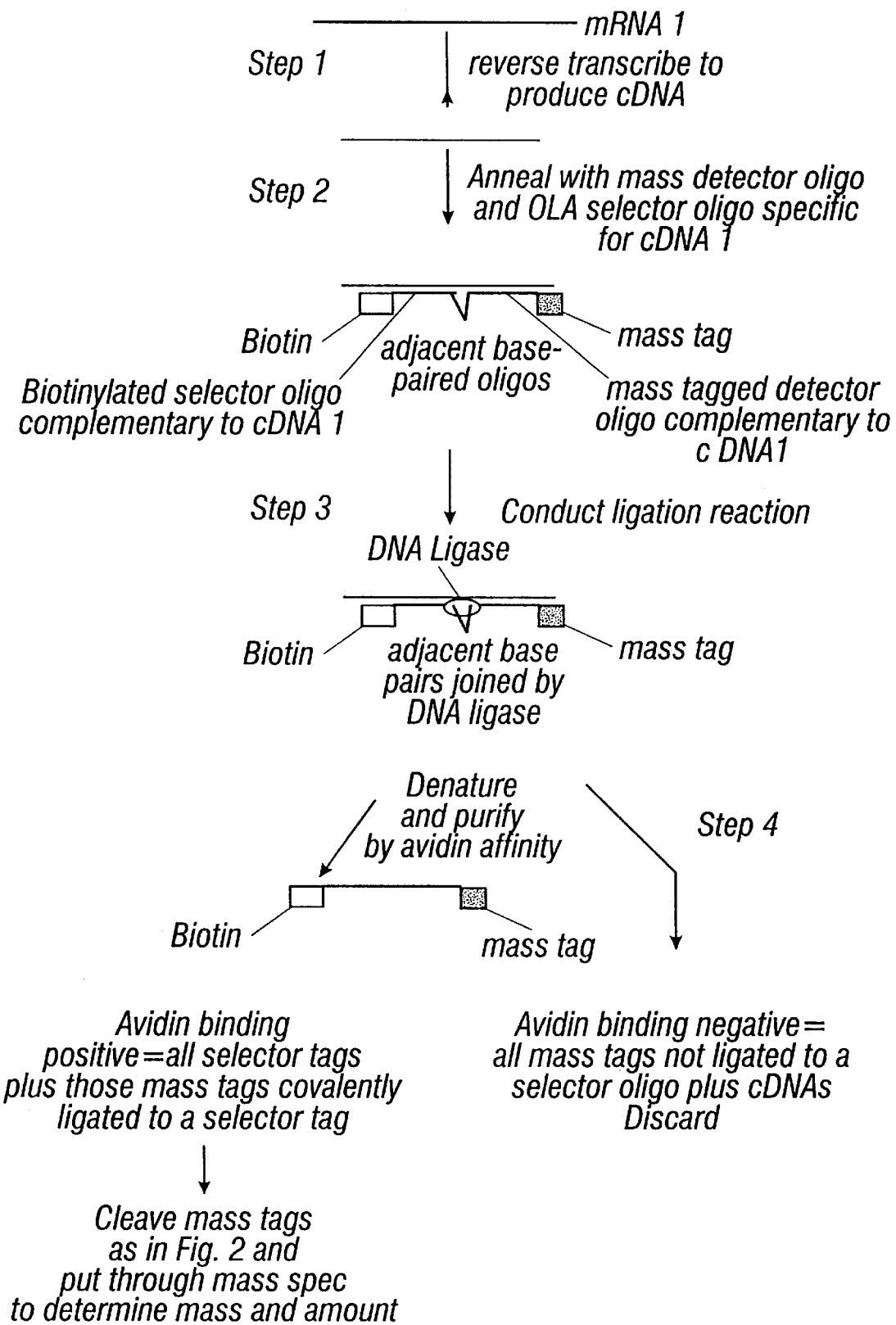
FIG. 3 shows a schematic drawing of a method of detecting a specific transcript using a detector oligonucleotide and a selector oligonucleotide. The detector oligonucleotide and selector oligonucleotide are linked by a ligation reaction.

The use of a selector primer along with a detector primer in a ligation reaction is shown schematically in FIG. 3. In FIG. 3, the target nucleic acid is a cDNA and the detector primers are DNA. However, any variation on DNA that can be used by DNA ligase can also be used as a substrate. Following hybridization to a cDNA with detector primers and with selector oligonucleotides, a reaction is performed on the mixture using DNA ligase as the catalyst. Such ligation reactions result in formation of a covalent phosphodiester link between the 3'-most residue of one oligo and the 5'-most residue of the adjacent annealed oligo or polynucleotide. The absolute and highly precise requirement for the placement of detector and selector oligonucleotides on the same target cDNA is extremely powerful for improving specificity of the reaction. Thus, the selector and detector oligonucleotides must be precisely adjacent relative to each other, and the nucleotides that are joined by ligase must be correctly base paired with the target cDNA. This requirement confers significant additional specificity to the detection method, compared with the hybridization of a single detector oligo by itself.

It is understood that this method can be varied by employing other oligonucleotide species, e.g., RNA or synthetic nucleic acids and corresponding ligases.

In another embodiment, the selector oligonucleotide and detector oligonucleotides are used as primers in a PCR reaction with a DNA polymerase, e.g., a thermostable DNA polymerase, to amplify a region in the target nucleic acid to obtain an amplification product. An advantage of using selector oligonucleotides and PCR to amplify the signal obtained using the detector primers is the increase in signal to noise ratio by requiring annealing of the selector primer at specified nearby sites. In addition, the absolute signal obtained will also increase. The latter increase in signal will come, though, at some cost in loss of quantitative fidelity.

Examples of selector oligonucleotides include; 1) biotinylating selector primers coupled with subsequent purification with avidin/strepavidin, or 2) labeling the selection primer with digoxygenin with subsequent purification with anti-digoxygenin affinity reagents, or 3) conjugating selector primers with any other physical or molecular tag. In the simplest case, the tags attached to the selection primers are general for all selection primers rather than specific for each target. However, for some applications, more than one family of selector oligonucleotides might be used in the same hybridization mix, either to act as an internal standard or for the purpose of generating more than one family of products for later detector tag analysis. i.e. multiplexing).

Any affinity scheme that allows physical isolation of selection oligonucleotides from non hybridized oligonucleotides can be used. However, the specificity using the selector oligonucleotide is enhanced only if the selector oligonucleotide and detector oligonucleotide are ultimately co-purified, or if a sequences complementary to the two oligonucleotides is generated, e.g., as in PCR.

In some embodiments, the tag on the selector oligonucleotide can be a fluorescent dye or dye-impregnated bead that would allow use of optical sorting to identify tagged oligonucleotides.

In another embodiment, the present invention provides a kit useful for detection of a specific nucleic acid in a collection of nucleic acids. The kit includes one or more containers comprising containing at least one oligonucleotide sequence covalently linked to a removable tag.

In yet another embodiment, the invention provides an isolated oligonucleotide composition comprising at least one oligonucleotide sequence covalently linked to a removable tag. The term "isolated" as used herein includes polynucleotides substantially free of other nucleic acids, proteins, lipids, carbohydrates or other materials with which they are naturally associated. cDNA is not naturally occurring as such, but rather is obtained via manipulation of a partially purified naturally occurring mRNA. Such compositions are useful for the identification of specific nucleic acids in a collection of nucleic acid sequences, e.g., corresponding to an expressed gene in a cell, tissue or cell extract.

Preferably the tag is detectable by mass spectroscopy. The composition in various embodiments may include 1 or 2 to 10, $10^2$, $10^3$, $10^4$, $10^5$, or $10^6$ or more different distinguishable tagged oligonucleotides. In various embodiments the composition includes about $1-10^6$, $10-10^5$, $10^2-10^4$, or $10^3-10^4$ oligonucleotide sequences. It is understood that the same tag be linked to distinct oligonucleotide sequences, provided that when the same tag is linked to more than one distinct oligonucleotide sequence, each oligonucleotide linked to the tag can be distinguished by the way in which the tag is attached to the oligonucleotide.

In some embodiments, at least a portion of the oligonucleotide sequence is complementary to a region of a transcribed gene.

Also included in the invention are isolated nucleic acids which include a sequence complementary to the oligonucleotide sequence of a tagged oligonucleotide.

Other Embodiments

It is to be understood that while the invention has been described in conjunction with the detailed description thereof, the foregoing description is intended to illustrate and not limit the scope of the invention, which is defined by the scope of the appended claims. For example, the molecular tags may be attached to nucleic acids longer than oligonucleotide, e.g., 100–1000 nucleotides in length, and used to identify homologous target sequences in a collection of nucleic acids. Other aspects, advantages, and modifications are within the scope of the following claims.

What is claimed is:

1. A method for detecting a first target nucleic acid molecule and a second target nucleic acid molecule in a collection of at least two nucleic acid molecules having different nucleotide sequences, the method comprising:

providing a first oligonucleotide covalently linked to a first removable tag by a first photocleavable linker, and a second oligonucleotide covalently linked to a second removable tag by a second photocleavable linker, wherein the first and second photocleavable linkers are cleavable at different wavelengths;

contacting the first oligonucleotide and the second oligonucleotide with the collection of nucleic acid molecules in a single reaction under conditions which permit hybridization of the first oligonucleotide and the second oligonucleotide to complementary sequences in the collection of nucleic acid molecules, thereby forming a mixture of hybridized and non-hybridized oligonucleotides;

separating hybridized oligonucleotides from non-hybridized oligonucleotides;

removing the first tag from hybridized first oligonucleotides by irradiating the mixture of hybridized and non-hybridized oligonucleotides at a first wavelength, thereby cleavinthe first photocleavable linker;

identifying the first tag by its known chemical property, thereby detecting the first target nucleic acid molecule;

removing the second tag from hybridized second oligonucleotides by irradiating the mixture of hybridized and non-hybridized oligonucleotides at a second wavelength, thereby cleaving the second photocleavable linker; and identifying the second tag by its known chemical property, thereby detecting the second target nucleic acid molecule in the collection of nucleic acid molecules.

2. The method of claim 1, wherein the contacting step is performed in solution.

3. The method of claim 1, wherein the contacting step is performed with the first oligonucleotide and the second oligonucleotide being attached to a solid support, or with the collection of nucleic acid molecules being attached to a solid support.

4. The method of claim 1, wherein the first oligonucleotide is about 8 to about 50 nucleotides in length.

5. The method of claim 1, wherein the first oligonucleotide is about 20 to about 40 nucleotides in length.

6. The method of claim 1, wherein the collection of nucleic acid molecules is selected from the group consisting of RNA and cDNA.

7. The method of claim 1, wherein the tag is identified from a method selected from the group consisting of mass spectra, emission spectra, absorption spectra, and antibody-binding.

8. The method of claim 1, wherein the tag is identified using a mass spectrophotometric method selected from the group consisting of time-of-flight, quadrupole, magnetic sector and ion trap mass spectrometry.

9. A kit useful for detection of the presence of a specific nucleic acid sequence in a collection of nucleic acid sequences, the kit comprising one or more containers comprising a first container containing a first isolated nucleic acid composition comprising a first oligonucleotide sequence covalently linked to a first removable tag by a first photocleavable linker and a second container containing a second oligonucleotide sequence covalently linked to a second removable tag by a second photocleavable linker, wherein the first and the second photocleavable linkers are cleavable at different wavelengths and a distinct correlation between the first photocleavable linker and the sequence of the first oligonucleotide is known, and a distinct correlation between the second photocleavable linker and the sequence of the second oligonucleotide is known.

10. The method of claim 1, wherein the amount of the identified first tag determines quantitatively the presence of the first target nucleic acid molecule identified from the collection of nucleic acids.

11. The method of claim 1, wherein the first removable tag is an amino acid, a peptide, a polymer, biotin, digoxygenin, a fluorescent dye or a dye impregnated bead.

12. The method of claim 1, where the first tag is identified by a method selected from the group consisting of absorption spectra, antibody binding and optical sorting.

13. The method of claim 1, wherein the first tag and the second tag are identical.

14. The method of claim 1, wherein the first tag and the second tag are different.

15. The method of claim 1, wherein the first oligonucleotide and the second oligonucleotide are complementary to a coding region of a transcribed gene.

16. The method of claim 1, wherein the first oligonucleotide and the second oligonucleotide are complementary to a coding region of the same transcribed gene.

* * * * *

SEQUENCE LISTING

<160> NUMBER OF SEQ ID NOS: 5

<210> SEQ ID NO 1
<211> LENGTH: 31
<212> TYPE: RNA
<213> ORGANISM: ARTIFICIAL
<220> FEATURE:
<223> OTHER INFORMATION: TARGET RNA 1

<400> SEQUENCE: 1
caugguagua guacgguacc gucuacggua a                                              31

<210> SEQ ID NO 2
<211> LENGTH: 30
<212> TYPE: RNA
<213> ORGANISM: ARTIFICIAL
<220> FEATURE:
<223> OTHER INFORMATION: TARGET RNA 2

<400> SEQUENCE: 2
uagcuuacac cuagggaccu auuucaggcu                                                30

<210> SEQ ID NO 3
<211> LENGTH: 18
<212> TYPE: DNA
<213> ORGANISM: ARTIFICIAL
<220> FEATURE:
<223> OTHER INFORMATION: DETECTOR OLIGO 1

<400> SEQUENCE: 3
tagtcggtac cgtactac                                                             18

<210> SEQ ID NO 4
<211> LENGTH: 18
<212> TYPE: DNA
<213> ORGANISM: ARTIFICIAL
<220> FEATURE:
<223> OTHER INFORMATION: DETECTOR OLIGO 2

<400> SEQUENCE: 4
gaaataggtc cctaggtg                                                             18

<210> SEQ ID NO 5
<211> LENGTH: 18
<212> TYPE: DNA
<213> ORGANISM: ARTIFICIAL
<220> FEATURE:
<223> OTHER INFORMATION: DETECTOR OLIGO 3

<400> SEQUENCE: 5
cggtattagg gcccagca                                                             18